(12) United States Patent
Wetzel et al.

(10) Patent No.: US 10,893,968 B2
(45) Date of Patent: Jan. 19, 2021

(54) ORTHOTICS HAVING RATE-RESPONSIVE, STRETCHABLE DEVICES

(71) Applicant: U.S. Army Research Laboratory, Adelphi, MD (US)

(72) Inventors: Eric D. Wetzel, Bel Air, MD (US); Joseph K. Hitt, Scottsdale, AZ (US); Robert B. Floersheim, West Chester, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 453 days.

(21) Appl. No.: 15/966,972

(22) Filed: Apr. 30, 2018

(65) Prior Publication Data
US 2018/0311064 A1    Nov. 1, 2018

Related U.S. Application Data

(63) Continuation-in-part of application No. 15/057,944, filed on Mar. 1, 2016, now Pat. No. 9,958,023, which
(Continued)

(51) Int. Cl.
*A61F 5/01* (2006.01)
*A61F 5/37* (2006.01)
(Continued)

(52) U.S. Cl.
CPC .............. *A61F 5/0123* (2013.01); *A61F 5/37* (2013.01); *A61F 5/0109* (2013.01);
(Continued)

(58) Field of Classification Search
CPC .. A61F 5/0123; A61F 5/37; A61F 2002/5066; A61F 2005/0197;
(Continued)

(56) References Cited

U.S. PATENT DOCUMENTS 5,712,011 A    1/1998  McMahon et al.
7,402,147 B1 *  7/2008  Allen ............... A61F 5/373
                                                   602/19
(Continued)

OTHER PUBLICATIONS

C Fischer, et al., "Dynamic properties of sandwich structures with integrated shear-thickening fluids," Smart Mater. Stuct. 15 (2006) 1467-1475.
(Continued)

*Primary Examiner* — Tarla R Patel
(74) *Attorney, Agent, or Firm* — Eric B. Compton

(57) ABSTRACT

Rate-dependent, elastically-deformable devices according to various embodiments can be stretched and recovered at low elongation rates. Yet they become stiff and resistive to stretching at high elongation rates. These device can be utilized in orthotics, braces, and circulation-enhancing compression garments for the prevention of injury, promotion of personal health, and/or enhancement in human performance. The rate-responsive properties of the devices are critical performance enablers, as they allow the devices to provide a unique balance of comfort and performance that cannot be achieved with conventional, passive straps, braces, and compression garments.

21 Claims, 9 Drawing Sheets

Related U.S. Application Data is a continuation of application No. 13/927,985, filed on Jun. 26, 2013, now Pat. No. 9,303,717.

(60) Provisional application No. 62/207,689, filed on Aug. 20, 2015, provisional application No. 61/670,430, filed on Jul. 11, 2012.

(51) Int. Cl.
*A61F 5/04* (2006.01)
*A61F 2/50* (2006.01)

(52) U.S. Cl.
CPC .............. *A61F 5/0111* (2013.01); *A61F 5/04* (2013.01); *A61F 2002/5066* (2013.01); *A61F 2005/0158* (2013.01); *A61F 2005/0167* (2013.01); *A61F 2005/0179* (2013.01); *A61F 2005/0197* (2013.01)

(58) Field of Classification Search
CPC .. A61F 2005/0158; A61F 5/0109; A61F 5/04; A61F 2005/0179; A61F 5/0111; A61F 2005/0167; A61F 13/04; A61B 17/60
See application file for complete search history.

(56) References Cited

U.S. PATENT DOCUMENTS

| | | | |
|---|---|---|---|
| 9,303,717 | B2 | 4/2016 | Wetzel et al. |
| 9,958,023 | B2 | 5/2018 | Wetzel et al. |
| 2006/0260027 | A1 | 11/2006 | Rhodes et al. |
| 2007/0246979 | A1 | 10/2007 | Browne et al. |
| 2017/0150767 | A1 | 6/2017 | Wetzel et al. |
| 2020/0163789 | A1* | 5/2020 | Tsunoda ................ A61F 5/0111 |

OTHER PUBLICATIONS

X Z Zhang, W H Li, and X L Gong, "The rheology of shear thickening fluid (STF) and the dynamic performance of an STF-filled damper," Smart Mater. Struct. 17 (2008) 035027.

Norman J. Wagner and John F. Brady "Shear thickening in colloidal dispersions," Phys. Today 62, 27 (2009).

M. A. Dawson et al., "The Dynamic Compressive Response of an Open-Cell Foam Impregnated With a Non-Newtonian Fluid," Journal of Applied Mechanics, 76 (2009), p. 061011.

M Soutrenon and V Michaud, "Impact properties of shear thickening fluid impregnated foams," Smart Mater. Struct. 23 (2014) 035022.

Paul T Nenno and Eric D Wetzel, "Design and properties of a rate-dependent 'dynamic ligament' containing shear thickening fluid," Smart Mater. Struct. 23 (2014) 125019.

DARPA, "Warrior Web to Prevent Injury, Reduce Effects of Load," Oct. 5, 2011. (Previsouly Available at: http://www.darpa.mil/NewsEvents/Releases/2011/10/05.aspx).

DARPA: Defense Sciences Office, "Warrior Web," Nov. 16, 2011. (Previously Available at: http://www.darpa.mil/Our_Work/DSO/Programs/Warrior_Web.aspx).

E.D. Wetzel, Y. S. Lee, R. G. Egres, K M. Kirkwood, J. E. Kirkwood, and N. J. Wagner. "The effect of rheological parameters on the ballistic properties of shear thickening fluid (STF)—Kevlar composites." Proceedings of Numiform 2004. Columbus, OH. p. 288-293. Jun. 13-17, 2004.

"Rate-dependent Extensional Tethers Using Shear Thickening Fluids," given at AFOSR 3rd Multifunctional Materials for Defense Workshop: Blurring the Distinction between Materials and Devices. Arlington, VA. Aug. 21, 2014.

Deborah A. Nawoczenski, MEd, PT, et al., "Objective Evaluation of Peroneal Response to Sudden Inversion Stress," JOSPT Nov. 1985, pp. 107-109.

Scott A. Lynch, MD, et al., "Electromyographic Latency Changes in the Ankle Musculature During Inversion Moments," The American Journal of Sports Medicine, vol. 24, No. 3, 1996.

Stephen B. Thacker, MD, et al., "The Prevention of Ankle Sprains in Sports a Systematic Review of the Literature," The American Journal of Sports Medicine, vol. 27, No. 6, 1999.

Umur Aydogan, MD et al., "Extensor Retinaculum Augmentation Reinforces Anterior Talofibular Ligament Repair," Clinical Orthopaedics and Related Research No. 442, pp. 210-215, 2006.

Daniel Tik-Pui Fong et al., "A Systematic Review on Ankle Injury and Ankle Sprain in Sports," Sports Med 2007; 37 (1): 73-94.

Victor Ibrahim, M.D., Zinovy Meyler, D.O., and Andre Panagos, M.D., ACSM Current Comment: "Ankle Sprains and the Athlete," American College of Sports Medicine, 2009.

Fong, D. et al., "Biomechanics of supination ankle sprain: a case report of an accidental injury event in the laboratory," American Journal of Sports Medicine, 37 (4), pp. 822-827, 2009.

Captain Brian R. Waterman, MD, Major Brett D. Owens, MD, Captain Shaunette Davey, DO, Captain Michael A. Zacchilli, MD, and Lieutenant Colonel Philip J. Belmont Jr., MD, "The Epidemiology of Ankle Sprains in the United States," J Bone Joint Surg Am. 2010: 92:2279-84.

Jeffrey D. Simpson et al., "The role of military footwear and workload on ground reaction forces during a simulated lateral ankle sprain mechanism," The Foot 34 (2018) 53-57.

U.S. Appl. No. 62/641,784, filed Mar. 12, 2018 titled "Rate-Activated Helmet Suspension," Eric D. Wetzel, Devon J. Spinelli, Thomas A. J. Plaisted.

* cited by examiner

Initial, Undeformed State of Device

State After Low-Rate Elongation of Device

State After High-Rate Elongation of Device

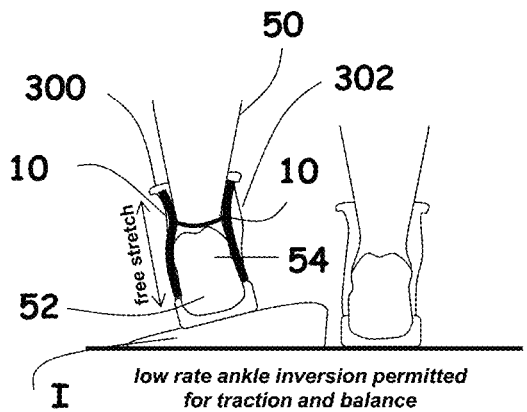
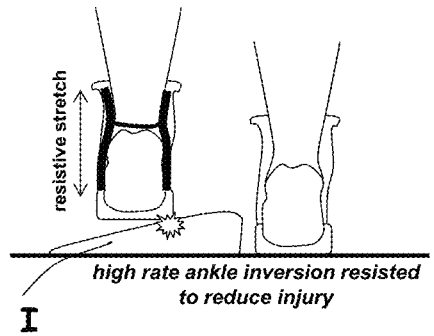
FIG. 4A — low rate ankle inversion permitted for traction and balance
FIG. 4B — high rate ankle inversion resisted to reduce injury
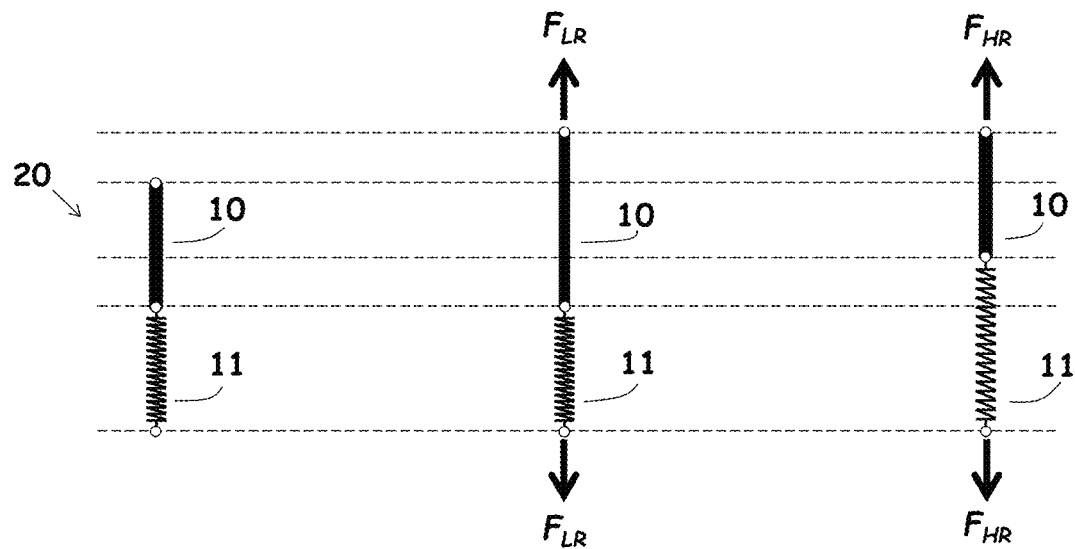
Initial, Undeformed State of Assembly | State After Low-Rate Elongation of Assembly | State After High-Rate Elongation of Assembly
FIG. 5A

ORTHOTICS HAVING RATE-RESPONSIVE, STRETCHABLE DEVICES

CROSS REFERENCE TO RELATED APPLICATION(S)

This application is a continuation in part (CIP) application of U.S. patent application Ser. No. 15/057,944 filed on Mar. 1, 2016. That application is a CIP of U.S. patent application Ser. No. 13/927,985 filed on Jun. 26, 2013, which in turn claims the benefit of U.S. Provisional Patent Application No. 61/670,430 filed on Jul. 11, 2012. Additionally, the '944 application claims the benefit of U.S. Provisional Patent Application No. 62/207,689 filed on Aug. 20, 2015. Each of the aforementioned patent applications is herein incorporated by reference in its entirety.

GOVERNMENT INTEREST

The invention described herein may be manufactured, used and licensed by or for the U.S. Government without the payment of royalties thereon.

Some of the research underlying the invention in this application resulted from collaborative research between the U.S. Army Research Laboratory (ARL) and GoXudio, LLC under the Cooperative Research and Development Agreement ARL CRADA 15-13-001.

BACKGROUND OF THE INVENTION

Field

Embodiments of the present invention generally relate to orthotics, and in particular to orthotics having rate-dependent, elastically-deformable devices.

Description of Related Art

Musculoskeletal injuries are a leading cause of medical treatment, lost duty time, and disability claims for both civilian and military personnel. Ankle, knee, and back injuries are particularly common sources of debilitating injury. A wide range of commercial products exist for the purpose of reducing the probability or severity of these injuries. These products include braces and orthotics with various straps, hinges, lever arms, and other mechanisms; compression garments to support body joints; athletic tapes or bandages, tightly wrapped around joints usually on the day of activity and destructively removed at the end of the duty day; or combinations of these approaches.

Each of these approaches suffer from various limitations. The most striking limitation is that there is little scientific evidence that any of these devices are effective at reducing injury rates or severity. Additionally, the devices can be highly uncomfortable, which can reduce user acceptance and wear rates and thereby limit a device's effectiveness. Finally, the bulk and mechanical restrictions of such devices can reduce human performance, or inadvertently increase the likelihood of other injuries. An improved wearable device such as a brace or orthotic is required that can effectively reduce the likelihood and/or severity of injury, without significantly reducing comfort or performance.

Compression garments, such as tight-fitting, elastic ankle braces, knee braces, and calf socks, are used for a range of health-promotion applications. The tight fit of compression garments in some cases are claimed to reduce joint injuries in a manner complementary to braces or orthotics, by holding joints and tissue together to reduce the likelihood of a deviation from normal kinesiological behavior. These claims have not yet been supported by scientific evidence. Compression garments are also believed to enhance circulation, adding external pressure to the extremities to drive blood back towards the heart, often against the resistance of gravity. Tighter compression with higher elastic resistance is believed to be more effective at enhancing circulation, but under constant stress the wearer can experience local irritation and overall discomfort. Improved compression garments that provide joint support, or enhance circulation, while remaining comfortable and not significantly reducing human performance, are needed.

Human performance enhancement is a critical goal for biomechanics researchers, the military, and athletes. Devices to enhance the energy efficiency of walking or running strides, in particular, are highly desired. Some approaches for enhancing stride efficiency have relied on sensors and actuators, which require a power source (such as a battery back), and tend to be unacceptably bulky, fragile, and expensive. A smart material approach that can enhance stride efficiency in an elegant, self-powered, and physically robust package is desirable.

SUMMARY OF THE INVENTION

Rate-dependent, elastically-deformable devices according to various embodiments can be stretched and recovered at low elongation rates. Yet they become stiff and resistive to stretching at high rates. According to embodiments, an apparatus may be formed of one or more rate-dependent, elastically-deformable devices. The apparatus may be configured as an orthotic device, brace, or circulation-enhancing compression garment in various embodiments.

As an ankle orthotic, in embodiments, at least one rate-dependent, elastically-deformable device may be configured to limit unwanted ankle supination. The rate-dependent, elastically-deformable device will couple the shank (or lower leg) and foot across the ankle joint. During slow, normal motion in daily and sporting activities, the rate-dependent, elastically-deformable device will not limit motion. It will not cause any weakening of the joint caused by accommodation to the brace over time. However, during fast motions, the device will limit the motion (e.g., supination) of the ankle.

As a knee orthotic, in embodiments, at least one rate-dependent, elastically-deformable device may be configured and used in conjunction with other elastic elements to enhance walking or running gait. The rate-dependent, elastically-deformable device will couple the shank and thigh (or upper leg) across the knee joint. Due to its speed-sensitive response, it can arranged in series or parallel with elastic elements to provide elastic resistance, storing and releasing energy in a manner than varies depending on the speed and rotation angle of the knee joint. Such an orthotic device can improve human biomechanics, for example by absorbing energy during one part of the stride and returning it to the body to enhance forward thrust during another part of the stride. The speed sensitivity of the device allows for the extent of elastic storage and release to be of one magnitude and timing during walking, and a different magnitude and timing during running.

As a lower leg compression orthotic, in embodiments, at least one rate-dependent, elastically-deformable device may be configured to mechanically enhance blood circulation. The device may be arranged around the calf muscle so that flexing of the calf muscle is resisted by the device, leading to compression on the calf and an increase in mechanical pressure that increases local venous pressure to assist in returning blood to the heart. Because of the speed-sensitivity of the device, general compression on the joint will be at a low, comfortable level during a relaxed state, but momentary bursts of high compression can be induced by voluntary calf muscle activation.

These and other embodiments will be described in further detail below with respect to the following figures.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. The drawings are not to scale unless so stated. It is to be noted, however, that the appended drawings illustrate only typical embodiments of this invention and are therefore not to be considered limiting of its scope, for the invention may admit to other equally effective embodiments. These embodiments are intended to be included within the following description and protected by the accompanying claims.

FIG. 1A shows the device at an initial, undeformed state, FIG. 1B shows the device in a state after slow elongation; and FIG. 1C shows the device in a state after rapid elongation.

FIG. 2A shows a plot of force versus displacement, and FIG. 2B shows a plot of force versus time, for different elongation rates.

FIG. 3A shows an elastic knee brace with small diameter devices arrayed on the knee brace to provide targeted reinforcement, and FIG. 3B shows a hinged knee brace in which a larger diameter device resists high rate bending.

FIGS. 4A and 4B illustrate an ankle brace including rate-dependent, elastically-deformable devices, and its operation, where FIG. 4A shows a situation of a person walking normal over an inclined surface, and FIG. 4B shows a situation of a quick, abrupt drop onto an inclined surface.

FIGS. 5A-5C illustrate a rate-dependent, elastically-deformable device combined with elastic elements, where FIG. 5A shows the behavior of a device in series with an elastic element; and FIG. 5B shows the behavior of a device in parallel with an elastic element; and FIG. 5C shows an assembly comprised of a high stiffness spring in series with a sub-assembly having a low stiffness spring in parallel with a device.

FIG. 6A shows a single rate-dependent, elastically-deformable device, FIG. 6B shows a rate-dependent, elastically-deformable device in series with a spring, FIG. 6C shows a rate-dependent, elastically-deformable device in parallel with a spring, and FIG. 6D shows a rate-dependent, elastically-deformable device in parallel with an inextensible cable.

in FIG. 11B two parallel devices are in series with an element that exhibit elastic bending response, such as a leaf spring, configured to resist knee flexure; and in FIG. 11C one device is in series with one longitudinally elastic spring, configured to resist knee extension.

FIG. 12B uses a device in series with a braided mesh sleeve that undergoes radial contraction when tensioned longitudinally; and FIG. 12C shows a long device in series with an athletic tape or bandage that is wrapped around the foot and ankle to induce calf pressure, in particular during foot extension and flexure.

DETAILED DESCRIPTION

Rate-dependent, elastically-deformable devices according to various embodiments can be stretched and recovered at low elongation rates. Yet they become stiff and resistive to stretching at high elongation rates.

Figure 1A:
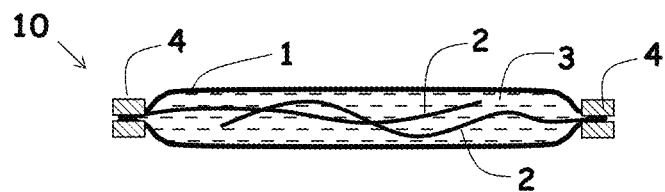
FIGS. 1A-1C illustrate schematics of one rate-dependent, elastically-deformable device, and its operation, according to one embodiment, where
Figure 1B:
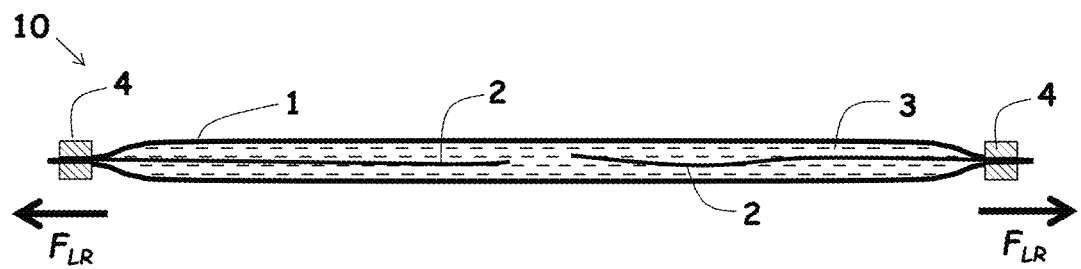
Figure 1C:
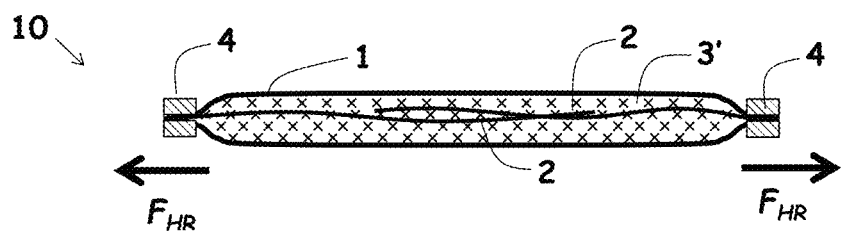

FIGS. 1A-1C illustrates one rate-dependent, elastically-deformable device 10 and its operation in accordance with one embodiment of the present invention. These figures show a cross-sectional cut-away view along the length of the device 10. In general, the rate-dependent, elastically-deformable device 10 includes an elastically-deformable confinement member 1 which houses one or more filaments 2, as well as a fluid 3 which substantially fills the remainder interior volume of the confinement member 1. The fluid 3 is sealed within the confinement member 1 by a crimp seal 4. The device 10 is configured to elongate or otherwise stretch by the application of an external tensile force applied at its ends. The rate-dependent, elastically-deformable devices 10 may also be referred to as rate-activated tethers (RAT).

The resistance force to extension of the device 1 is designed and configured to increase as the rate of extension or rate of elongation of the device 10 increases. The extension rate or elongation rate of the device can be expressed, for example, as a relative elongation of the device as a function of time or the speed/velocity of the device at one of its ends which displaces with respect to the other. These rates may be measured in units such as meters/sec, inches/sec, mm/sec, etc., although the extension or elongation rate might also be expressed as a dimensionless strain value (e.g., elongation of the device normalized by the initial device length) as a function of time. This may be expressed in units of $s^{-1}$. Other conventions might also be used for extension or elongation rates. It should also be appreciated that the terms low-rate elongation and high-rate elongation as used herein may be relative to a particular embodiment or application. Put another way, what may be a low rate of elongation for one application may not be a low rate of elongation for another application. Similarly, what may be a high rate of elongation for one application may not be a high rate of elongation for a different application. Thus, a key feature of the innovative technology is the ability to judiciously tailor or otherwise configure the elongation rate response of individual devices to any particular application.

FIG. 1A shows the device 10 in an initial undeformed state with no external tensile force applied. The elastically-deformable confinement member 1 may be formed of rubber, silicone, elastomer, fluoroelastomer (such as sold under the tradename Viton®), urethane, natural latex, synthetic latex, thermoplastic elastomer, polymer, or the like, which generally are elastic and resilient and capable of confining a fluid therein. Latex may be stretchier than some of the other materials, but is also more porous to certain materials. The fluid 3 may be confined to interior of the elastically-deformable confinement member 1 by crimps, plugs, melted (heat-crimped) ends, glues or adhesives (such as thermoplastic or thermoset resins) provided at the ends of the elastically-deformable confinement member 1.

In one embodiment, the elastically-deformable confinement member 1 may be formed of a stretchable elastic tube. The use of an elastic tube enables flexibility of the device 10 in multiple directions. For some applications, the tube may have an inner diameter of about 0.01-100 mm, or more preferably 0.1-10 mm in an initial undeformed state. The tube may generally have a circular cross-sectional shape for many applications, but it should be appreciated that other cross-sectional shapes are also possible, such as rectangular, square, hexagonal, etc.

The elastically-deformable confinement member 1 might also be formed into a planar shape, for example, formed by sealing the edges of two sheets of elastomeric materials to form an elastomeric membrane. This elastomeric body could be shaped like a square sheet, round membrane, or arbitrarily-shaped body. An array of filaments 2 could be enclosed in this elastomeric body, and with the filaments aligned in parallel, orthogonally, or in any arbitrary combination of in-plane orientations. The precise shape of the body and the orientation of the filaments 2 will be dictated by the application. It should be appreciated that other stretchable configurations are also possible. For instance, the outer confinement member 1 could be formed (or partially formed along its length) of spiral wound or folded material which can elongate linearly when stretched, like a bellows, for example.

To prevent puncturing by the enclosed filaments 2, the elastically-deformable confinement member 1 may formed of a reasonable thickness whether formed of one layer or formed of multiple layers. Wire mesh or fibers might further be incorporated into the walls of the elastically-deformable confinement member 1 for this purpose. In addition, to enhance sliding of the filaments 2 relative to the elastically-deformable confinement member 1, interior surfaces of the elastically-deformable confinement member 1 may be further provided with a low-friction coating or layer of material, such as Teflon®.

The filaments 2 may include be formed of wire, cable, ribbon, band, thread, cord or the like, of steel, polymer, glass, carbon or other appropriate material for this purpose. The filaments 2 may be flexible to provide flexibility of the device 10 as well, but need not be flexible for all embodiments. The filaments 2 may be monofilament or multifilament, twisted, untwisted or braided. In one embodiment, the filaments are flat, flexible elements, such as ribbons. And a pair of ribbons may be provided with ones of the pair being connected to opposite ends of the elastically-deformable confinement member 1 in some instances. The ribbons may be formed of strip-shaped materials formed of nylon or metal, for example. There are certain advantages to using flat ribbons including (i) there is more shear area between a pair of ribbons, as compared to a pair of round cables, so that higher force resistance to elongation is possible, and (ii) ribbons can be stiffer than cables so the ribbon-based device recovers from its stretched state (i.e. relaxes) faster than a cable-based device.

In the preferred embodiment, one end of each and every filament 2 may be coupled to the elastically-deformable confinement member 1, preferably at or near its ends. To this end, the filaments 2 may be mechanically and/or adhesively coupled to the confinement member 1. For mechanical attachment, a crimp, clamp, spring clip, threaded fastener, snap-on fastener, stitch, and/or the like may be used. FIGS. 1A-1C illustrate the device 10 having filaments 2 coupled to the ends of the elastically-deformable confinement member 1 by a crimp seal 4. For adhesive coupling, various thermosetting or thermoplastic (heat-setting) glues and adhesive may be used, including hot-melt, urethane, silicone, epoxy, acrylate, or the like, as some examples. If the filaments 2 are themselves readily stretchable or elastic, both of their ends could be coupled to opposite ends of the elastically-deformable confinement member 1 so as to stretch along with the elastically-deformable confinement member 1.

In another embodiment, one or more filaments 2 in the device could be unconstrained to the confinement member 1. These filaments would be freely floating in the device, but would provide some mechanical or viscous coupling to other filaments 2 during device extension.

End effectors (not shown) may be coupled to or otherwise provide mounting points on the ends of member 1 which may used to connect the device 10 to other systems such as mechanical linkages. Depending of the application, the end effector mounting may be permanent or readily removable. Such end effectors may include, for instance, threaded attachment (e.g., via screws or eyehooks), clips, clasps, buckles, snaps, buttons, straps, knots, stitches/stitching, staples, hooked fasteners, clamps, cotter pins, nails, glue/adhesives, or the like.

For some applications, the filaments 2 may have an outer diameter of about 0.01-10 mm in diameter, or more preferably 0.1-1 mm. Smaller and larger filaments might also be used for other applications. In order to inhibit their puncturing through the outer confinement member 1, the filaments 2, and particularly their ends, may be modified. For example, filament modifications may include rigid, smooth balls; soft coatings; filament loops; low-friction coatings; guide bushings or washers; chamfering; or compression sleeves. Grinding, sanding, or soldering may also be used to blunt or dull the tips the filaments 2 to inhibit puncturing through the confinement member 1.

Generally speaking, the filaments 2 should have some degree of stiffness for effective operation of the device 10. For example, the filaments 2 may be "push-pull" cables. By push-pull, it is meant that the filament 2 can readily be pushed and pulled through the fluid 3. Most filaments are sufficient to be pulled through a fluid because the drag between the filament and fluid tends to keep the filament in a state of tension generally unfurling the filament. However, when pushed through the fluid, the viscosity of the fluid tends to keep the filament in a state of compression. Thus, a very thin flexible thread might not be an effective filament because it may buckle, ball-up, or tangle-up due to compressive forces between the filament and the fluid when the device retracts. To increase shearing of the fluid 3, the filaments 2 may further include one or more crimps, barb, ridges, waved surfaces (e.g., square, triangular, sawtooth or sinusoidal shaped surfaces), etc. Also, the filaments 2 might be arranged in a helical (or "corkscrew") arrangement to encourage entanglement.

One important aspect of the invention is that the resistance force to extension of the device changes, and in particular, increases as the extension rate of the device increases through the use the fluid 3. The fluid 3 may be selected so as to change its rheological properties as the rate of extension of the device changes. For example, the device 10 may be designed so as to have a predetermined threshold rate of extension in which such a change occurs. Thus, at low rates below the threshold, the filaments 2 can readily slide through the fluid 3 and/or past each other. Yet at high rates above the threshold, the fluid 3 transforms to a more rigid material or higher viscosity fluid which greatly reduces or prevents movement of the filaments 2 through the fluid 3 and producing a stiff linear element. Put another way, the device 10 may be thought of as being easily stretchable at low elongation rates, but "stiffens" or "locks up" (i.e., rigidly resists or substantially prevents any further deformation) when pulled quickly at high elongation rates.

The fluid 3 substantially fills the remaining volume inside the elastically-deformable confinement member 1 once the filaments 2 are installed therein. The fluid 3 may be a Newtonian or non-Newtonian fluid. Newtonian fluids have a viscosity that will change with temperature, but do not change with the strain rate. By contrast, non-Newtonian fluids have a viscosity that changes with the strain rate which may enable devices to be more tailored for certain operational performance.

In some embodiment, fluid 3 may be a shear thickening fluids (STFs). STFs, one type of non-Newtonian fluid, are materials that flow like a liquid at low deformation rates, but become highly resistant to flow at high deformation rates. Exemplary thickening fluids which may be used in accordance with the embodiments of the present invention are disclosed in Norman J. Wagner and John F. Brady "Shear thickening in colloidal dispersions," Phys. Today 62, 27 (2009), herein incorporated by reference. Stretching the device 10 at low rates does not transition the STF, and the filaments 2 are free to move through the fluid 3 and slide past each other. If, instead, the device 10 is pulled quickly, high shear rates develop between the filaments and the STF material hardens, binding the filaments together and providing high resistance to elongation or a stiff, generally unstretchable device state. Relaxation of the force induces the STF to return to a flowable state, and the device once again becomes stretchable. By using a Newtonian fluid, rather than a true shear thickening fluid, one can get a useful rate-dependent response, although the rate-dependence of the response is not nearly as severe or drastic as devices containing an STF. The ideal rate-dependent response of a device depends on the application. For some applications, severe stiffening may be desirable to "lock" the device and prevent further motion. In other applications, a "locked" response may create an undesirably severe effect; instead, a device that is still extensible, but at considerably higher elongation forces, might be more desirable. The properties of fluid 3 can be tailored to provide the desired device response.

In some embodiments, the fluid 3 may be a suspension of solid particles in a liquid (which may also be referred to as a carrier fluid or carrier liquid). For example, the suspension may be formed of colloidal particles generally nano-sized (i.e. 1-1000 nm). Colloidal refers to the fact that the particles are intact solid particles, they may not dissolve in the liquid, and they are generally stabilized in the liquid so that they do not agglomerate, settle, or float to the surface of the liquid system over short periods of time (i.e. they are stable for days, weeks, or longer). However, devices 10 may be constructed with a fluid 3 that is a suspension of larger size solid particles (i.e. 10-1000 µm, or even larger), which do not dissolve in the liquid and are generally stable in the liquid too. In these devices, the fluid is technically not a colloid. The term "suspension" as used herein is intended to encompass both colloids and suspensions of larger size solid particles in a liquid.

Depending on the type of particles and liquid, and the desired non-Newtonian response, the solid particles may constitute 10-70% by volume of the fluid 3; more preferably, the solid particles constitute 30-60% by volume of the fluid 3. For examples, a preferred volume fraction for spherical particles is around 50% by volume; a preferred volume fraction for high aspect ratio precipitated calcium carbonate particle may be as low as 35% The liquid could be water, oil, a polymeric liquid, a glycol, a fluorofluid, or glycerin, for example. The colloidal particles may be composed of ceramics, polymers (such as poly(methyl methacrylate) (PMMA) or polystyrene), or metals. Or, they may comprise of silica, alumina, titania, clay, precipitated calcium carbonate, or ground calcium carbonate. It is believed that precipitated calcium carbonate is more likely to be stable than ground calcium carbonate in some instances. One or more additional additives might also be included in the fluid 3 which function as stabilizers, emulsifiers, surfactants, pigments, etc. The fluid 3 may also include gels, gums, and putties.

In other embodiments, the fluid 3 may be an electrorheological fluid, or a magnetorheological fluid. Electrorheological fluids include a suspension of extremely fine non-conducting particles (e.g., up to 50 micrometers diameter) in an electrically insulating fluid. The viscosity of these fluids can change reversibly (e.g., an order of up to 100,000) in response to an electric field. Magnetorheological fluids include a suspension of fine ferromagnetic particles in a liquid. When subjected to a magnetic field, the fluid greatly increases its viscosity, to the point of becoming a viscoelastic solid. In the case of using an electrorheological fluid, a voltage may be applied to the fluid 3 by using a voltage-generating device with opposite electrodes attached to filaments at opposite ends of the device; thus creating an electric field across the fluid 3 that would trigger a thickening response in the fluid. Similarly, in the case of using a magnetorheological fluid, a magnetic-field-generating device provided in the vicinity of the fluid 3 (for example, using an electromagnet) generates a magnetic field to the fluid 3 such that the fluid 3 can increase in viscosity or transition to a non-flowable state. Suitable microcontrollers, which may include known feedback or feedforward control algorithms, may be further provided to control the voltage-generating device and magnetic-field-generating device thus providing a desired fluid response.

When the device 10 is subjected to an external tensile force, the elastically-deformable confinement member 1 elongates, and the one or more filaments 2 are pulled or dragged through the fluid 3 as it stretches. The relevant movement of the filaments 2 through the fluid 3 creates shearing flow(s) in the fluid 3. Some shearing flow may also be created by relevant movement of the fluid 3 and the interior surface(s) of the elastically-deformable confinement member 1 and/or within the fluid 3 itself. The shearing flow of the fluid 3 creates a force within the device 10 which tends to resist the external tensile force that is elongating the elastically-deformable confinement member 1.

In general, the resistive force due to the shearing flow of the fluid 3 is largely dependent on the speed or rate of elongation/stretching of the elastically-deformable confinement member 1, the surface area of the filaments 2, and/or the spacing of the filaments 2 between one another and the interior surface(s) of the elastically-deformable confinement member 1. Other factors may also influence the resistive force, such the cross-sectional shape of the elastically-deformable confinement member 1, the shape of the filaments 2, and/or the viscosity of the fluid 3, for instance.

FIG. 1A shows the rate-dependent, elastically deformable device 10 in an undeformed state. The elastically-deformable confinement member 1 here is in an initial, undeformed state.

As illustrated in FIG. 1B, stretching the device 10 with an external tensile force $F_{LR}$ in an attempt to impose low-rate elongation does not create sufficient resistance force in the device 10, such that the filaments 2 are free to readily be pulled through the fluid 3 and/or slide past each other. Here, the elastically-deformable confinement member 1 has been stretched and the filaments 2 have been pulled and straightened somewhat and slid past each other. The fluid 3 remains in a flowable state similar to that of the device 10 in its initial undeformed state. Upon gradual release of the external tensile force $F_{LR}$, the elastically-deformable confinement member 1 tends to return to its initial undeformed shape and length as shown in FIG. 1A.

On the other hand, stretching the device 10 with external tensile force $F_{HR}$ in an attempt to impose high-rate elongation, as illustrated in FIG. 1C, changes the operable characteristics of the elastically-deformable device 10. For instance, if the device 10 is pulled quickly and elongates at a high rate, high shearing rates develop between the elastically-deformable confinement member 1, the filaments 2 and the fluid 3. The high shearing rates cause the fluid 3 to generate a high resistance force in the device 10, preventing the filaments 2 from readily sliding through the fluid 3 and/or past each other. The elastically-deformable confinement member 1 has stretched a small amount, and the filaments 2 have straightened slightly. Due to the high shearing of the fluid 3, the fluid 3 has now transformed into a more rigid-state material 3'. The filaments 2 are no longer free to readily slide past one another. This results in the device 10 transitioning to a device that is highly resistant to elongation, or becomes so resistant to elongation so as to become unstretchable. The device 10 will remain in the stiffened state as long as force is being applied to the ends of the device. If the force is relaxed, the fluid 3' will return to a flowable state like fluid 3, and the device 10 will gradually reduce in length back to the initial, undeformed state of the material shown in FIG. 1A.

Figure 2A:
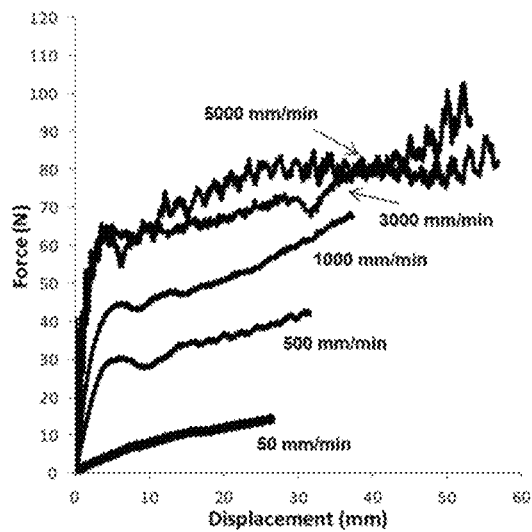
FIGS. 2A and 2B illustrate experimental measurements of force versus displacement for one rate-dependent, elastically-deformable device pulled at different elongation rates, demonstrating the rate-dependent resistance to extension, where
Figure 2B:
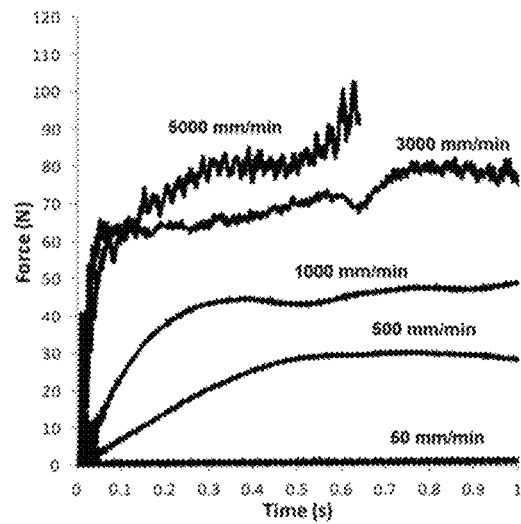

FIGS. 2A and 2B show experimental force measurements during elongation of a prototype device stretched at different rates. The elongation rates were 50 mm/min, 500 mm/min, 1,000 mm/mm, 3,000 mm/min and 5,000 mm/min. The device gage length in these experiments was 152 mm, so these deformation rates correspond to strain rates of 0.0055, 0.055, 0.11, 0.33, and 0.55 $s^{-1}$, respectively. FIG. 2A shows a plot of force versus displacement, and FIG. 2B shows a plot of force versus time, for these elongation rates.

The force versus displacement plot FIG. 2A demonstrates the rate-sensitive response of the device. The liquid here was a STF which was formulated by blending 450-nm-diameter silica and ethylene glycol (EG) at a mass ratio of 1.92 g silica: 1 g EG. The STF was dispersed using a rolling jar mixer over a period of 24 hours. The STF was then placed inside a 6.35-mm-ID, 7.9375-mm-OD Viton® tube with nylon end caps and 0.794-mm-diameter stainless steel wire rope with compression sleeves on the end. The tubing was filled with shear thickening fluid by partially clamping one end of the tubing with surgical tubing forceps while slowly pouring the fluid in until the fluid reached the surgical forceps. In some cases, it was helpful to apply low amounts of heat using a heat gun or to inject the fluid using a 3-mL syringe. The surgical forceps were removed and then the tubing was plugged at one end using the nylon plugs with attached wires described above. At this point, the tube was gently massaged to push air bubbles to the top of the tube and more fluid was added in order to fill the void space previously occupied by the air bubbles. Afterwards, the second nylon plug was inserted into the tubing.

The force versus time plot FIG. 2B shows that the devices respond very rapidly, with the high rate plateau force reached in less than 100 ms after force application. This rapid response means that there would be very little lag time between application of high elongation rate, and transformation of the device to a more resistive state.

As apparent, at the low elongation rates, the device provides very little resistance to stretching. One the other hand, as elongation rate increases, the resistance to deformation (force values during extension) increases. Comparing the highest rate response to the lowest rate response at 100 ms, the resistive force at high rate is approximately 100× higher than the resistive force at low rate. These particular embodiments of the device show a resistive force that peaks and then plateaus, which could be a beneficial feature of a device. For example, the long plateau force indicates high energy absorption during elongation. Also note that if the device is elongated at high rates, but the available elongation force is less than the plateau force, the device would essentially feel unstretchable and provide a rigid response. Other devices can be engineered with considerably higher resistive forces, and resistive forces that do not plateau but reach a limiting displacement beyond which further elongation would require exceedingly high forces.

The device tested was designed to provide much higher resistance to elongation as the elongation rate increases. But it was not designed to rigidly lock-up at high rates of elongation (rather, some elongation continued at higher rates of elongation just at much smaller degree). The device nonetheless still appeared to lock-up if the force applied is less than the plateau force. While rigid locking-up of the device may be useful for some applications, for other applications a rigid locking effect would be too severe a response, and a higher elongation force is a preferred response.

According to various embodiments of the present invention, one or more rate-dependent, elastically-deformable devices may be incorporated into various devices and apparatuses to provide rate-dependent operational performance. For example, in some embodiments, one or more rate-dependent, elastically-deformable devices may be incorporated into an apparatus such as an orthotic device to create rate dependent braces. Exemplary orthotic device which may be benefited in the manner may include, for example, head and helmet braces, knee braces, ankle braces, back braces, neck braces, wrist braces, slings, and other orthotic devices. The rate-dependent, elastically-deformable devices may also be provided in other wearable equipment, such as shoes, boots, headgear, belts, harnesses, or the like. This technology presents a new approach and, thus orthotic devices that can provide higher resistance to motion during higher speed events which a soldier or athlete may encounter. These new and improved devices will be more effective at resisting unplanned loads and preventing injuries. Many joint injuries associated with rapid twisting and translations of limbs and joints, such as slipping, stepping in a hole, landing from a jump, or planting a foot while changing direction may be prevented. In other embodiments, one or more rate-dependent, elastically-deformable devices may be incorporated into safety equipment, sporting/athletic equipment and goods, robotics, restraints (e.g., seat-belts) and mechanical assemblies. According, various applications, such as, linkages, vehicle suspension systems, robotics, "strapping" (e.g., bungee-type cords, self-tightening straps, etc.) clothing and woven textiles may be benefited. One device might be used as a replacement for a simple Velcro® or an elastic strap.

Figure 3A:
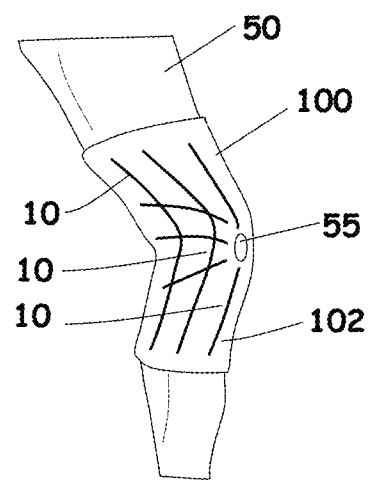
FIGS. 3A and 3B illustrate two knee braces including rate-dependent, elastically-deformable devices, where
Figure 3B:
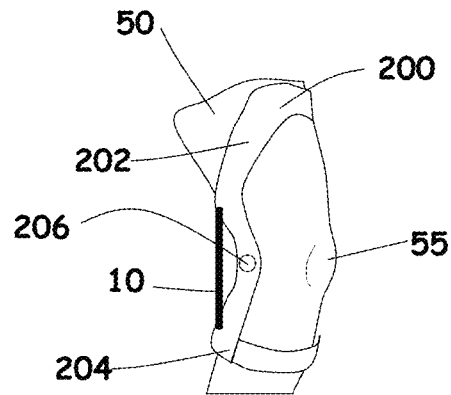

The next figures show examples of various orthotic devices according to embodiments of the present invention. In FIGS. 3A and 3B, the orthotic devices are knee braces which are configured to be worn on a person's leg 50 on the knee 55 to provide increase support and/or stability for the knee 55. The precise number of elongational devices 10 that are incorporated into the knee braces, and the orientation of these devices relative to knee physiology or desired kinesiology for a given activity or injury risk, could be tailored to a particular application. The knee braces are designed to permit normal walking and other activities, but stiffen and resist deformation during high rate events, like landing from a jump. Moreover, the knee braces provide rate-dependent operational performance not found in conventional braces.

FIG. 3A shows an elastic knee brace 100 according to one embodiment. The knee brace 100 includes multiple rate-dependent, elastically-deformable devices 10 that are fastened to, bonded to, woven into, and/or otherwise attached to the body 102 of the knee brace 100. The body 102 may be formed of a conventional elastic fabric textile, such as sold under the tradename Spandex®. Or the body 102 may be formed of a rigid or semi-rigid material which comports to the curvature of the leg 50 or foot 52 as generally known. When worn, the body 102 snugly engages the leg 50 and knee 55 and holds the knee brace 100 in place. Adjustment straps (not shown) having buckles or hook and loop type (e.g., Velcro®) fastening may be further included to better couple the brace 100 to the leg 50 and knee 55. To facilitate incorporation into the fabric of the body 102, the devices 10 may have a small outer diameter, such as 0.1-10 mm.

FIG. 3B shows a hinged knee brace 200 according to another embodiment. The knee brace 200 body includes an upper portion 202 worn above the knee 55 and a lower portion 204 worn below the knee 55. The upper and lower portions 202, 204 are coupled with a pivot 206 to provide hinged movement of the brace 200 at the knee 55.

The upper and lower portions 202, 204 may be formed of a conventional elastic fabric textile. Or they may be formed of a rigid or semi-rigid material which comports to the curvature of the leg 50 and knee 55 as generally known. When worn, the upper and lower portions 202, 204 of the brace 200 snugly engage the knee 55 and holds the knee brace 200 in place on the person's leg 50. Adjustment straps (not shown) having buckles or hook and loop type (e.g., Velcro®) fastening may be further included to better couple the brace 200 to the leg 50 and knee 55.

The knee brace 200 further include one or more rate-dependent, elastically-deformable devices 10 which couple to the upper and lower portions 202, 204 of the brace 200. As shown, one rate-dependent, elastically-deformable device 10 externally couples those elements behind in the rear of the knee 55. Because of the greater forces the device 10 may be subject to in this orientation, it may have a large diameter, such as 1-20 mm. The device(s) 10 stretches freely during normal motion of the hinged knee brace 200, but becomes rigid during high rate motions that may cause injury.

The lengths, positions, number, orientations and/or operational characteristics of the devices 10 in the knee braces 100 and 200 are strategically designed to provide optimal support. The devices 10 incorporated into the braces 100 or 200 may have different characteristics. As shown in FIGS. 3A and 3B, the rate-dependent, elastically-deformable device(s) 10 may be positioned in a generally parallel orientation parallel to the length of the leg 50 in both of these knee brace embodiments. However, the devices 10 may be additionally or alternatively oriented generally orthogonally to the length of the leg 50, and/or at some angle thereto. Also, the devices 10 might further be oriented in a "criss-cross shape" or "X-shape" to provide greater lateral support to the knee 55. Other configurations are also possible. Under normal walking conditions, the elements of the devices 10 deform passively and do not resist motion. Under high loading rate, potentially injurious conditions, such as a knee hyperextension or knee twist during slippage, the devices become rigid and greatly limit or preferably prevent further motion of the knee 55.

FIGS. 4A and 4B show an ankle brace 300 and its operation, according to an embodiment. The ankle brace 300 includes multiple rate-dependent, elastically-deformable devices 10 that are fastened to, bonded to, woven into, and/or otherwise attached to the body 302 of the brace 300.

The body 302 may be formed of a conventional elastic fabric textile. Or the body 302 may be formed of rigid or semi-rigid material which comports to the curvature of the leg 50, foot 52 or ankle 54 as generally known. When worn, the body 302 snugly engages the leg 50, foot 52 and ankle 54 and holds the ankle brace 300 in place. Adjustment straps (not shown) having buckles or hook and loop type (e.g., Velcro®) fastening may be further included to better couple the brace 300 to the leg 50, foot 52 and ankle 54. These devices 10 enable low rate extension but prevent higher rates of extension and rotation of the ankle brace 300.

FIG. 4A shows a situation of a person walking normal over an inclined surface I. In this situation, the person's foot 52 (on the left) needs to rotate slightly with respect to the person's leg 50 for traction and balance. In this situation, the ankle brace 300 is configured to permit a low rate of inversion of the ankle 54 and foot 52 which is typically expected for walking. During the normal gait cycle, the foot both pronates and supinates. Pronation is a combination of three ankle movements, abduction, eversion, and dorsiflexion, while supination is combination of adduction, inversion, and planar flexion. When the foot hits the ground, the ankle pronates to absorb the shock, and when it pushes off, the ankle supinates.

FIG. 4B shows a situation of a quick, abrupt drop onto an inclined surface I. It is noted that alike elements to those in FIG. 4A are shown here, and will be referenced. Typically, in this situation, the person is not expecting this drop. This may occur for example when one inadvertently steps off a curb. And, because the person is not expecting the drop, the high rate of ankle inversion associated with the landing onto the incline surface I ordinarily (without the aid of the ankle brace 300) may cause injury to the person, such as an ankle sprain, or worse yet, possibly a break. It is noted that 70-80% of typical ankle sprains are caused by ankle inversion, whereas a smaller percentage is caused by ankle eversion. But, by wearing ankle brace 300, the ankle brace 300 advantageously resists the high rate of ankle inversion to reduce injury in this situation.

The rate-dependent, elastically-deformable devices 10 can be used in conjunction with elastic bands, springs, and tape. For example, a rate-dependent, elastically-deformable device 10 can be used in series with a spring. FIG. 5A shows an assembly 20 of one device 10 in series with a spring 11. The spring 11 may be a helical wound spring, for instance. When the combined assembly 20 is pulled slowly, the device 10 stretches and the spring 11 stays in a relaxed state and does not store energy. However, when the combined assembly 20 is pulled quickly, at a much faster rate, the device 10 resists the movement and the spring is stretched, storing energy. In this case, the device 10 is functioning like a rate-responsive clutch turning on or off the spring 11 mounted in series. The overall assembly 20 requires a higher force $F_{HR}$ to elongate during high rate extension, compared to the force $F_{LR}$ required to elongate during low rate extension.

Figure 5B:
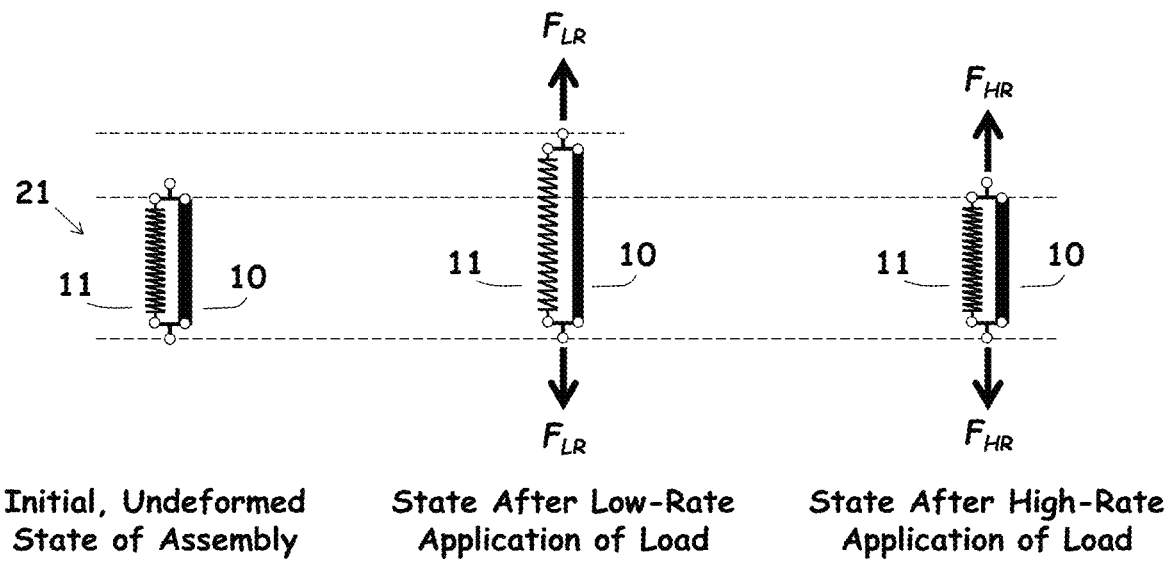

If a rate-dependent, elastically-deformable device 10 is mounted in parallel with a spring, the amount of stretch and overall stiffness can be adjusted. FIG. 5B shows an assembly 21 of one device 10 in parallel with a spring 11. When the combined unit is pulled slowly, the device 10 stretches with low resistance, and most of the energy of motion is stored elastically in the spring 11. When the combined assembly 21 is pulled quickly, at a much faster rate, the device 10 resists with high force, and absorbs high energy over short distances, reducing the total extent of stretch. When the loading arises for biomechanical motion, such as a swinging leg during walking, the amount of system energy stored in the spring will be higher during low rate action compared to high rate action.

Figure 5C:
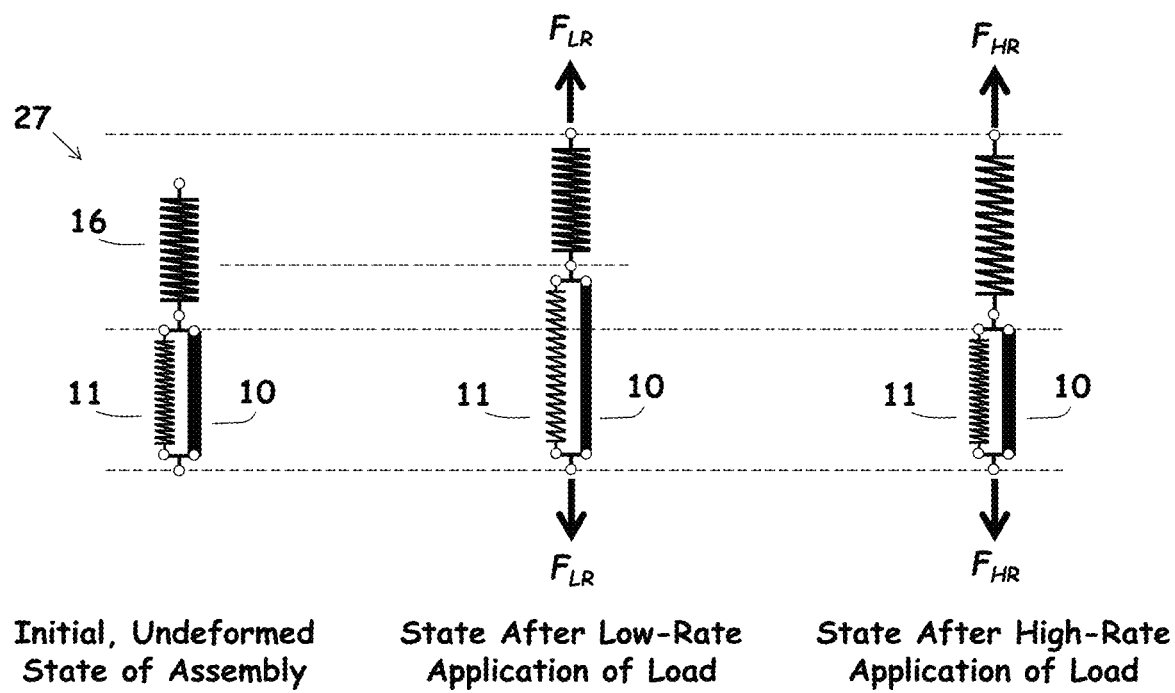

One or more rate-dependent, elastically-deformable devices 10 can be mounted in any combination of series and parallel structures with multiple spring 11 units. Various types of spring 11 may be used, such as helical, leaf, torsion, compression, etc., to provide even greater versatility. The overall combined structure will be tuned for the application. For example, FIG. 5C shows an assembly 27 having a low stiffness spring 11 in parallel with one device 10, which in turn are in series with a high stiffness spring 16. When loaded slowly, the assembly 27 will exhibit a low spring constant determined by the low stiffness spring. When loaded quickly, the device 10 will prevent loading of the low stiffness spring, leading to extension of the high stiffness spring 16. The total assembly 27 effectively exhibits an elastic response with speed sensitivity, that is, a lower stiffness at low elongation rates and a higher stiffness at high elongation rates. This property can be used to store and release mechanical energy with a response that is tuned for different extension velocities.

For braces and orthotics, the rate-dependent, elastically-deformable devices 10 can provide a number of advantageous features. Using an ankle brace as an example, the most common ankle injury is supination (outward rolling). It is desired to allow general, voluntary supination while restricting unwanted supination that can lead to injury. Voluntary supination is required, for example, to allow ankle rotation when walking over rough terrain or changing directions during sports. An orthotic using rate-dependent, elastically-deformable device(s) 10 to resist supination has the important property that lower speed rotations, such as those associated with voluntary action, are not resisted significantly; while, in contrast, the high speed supinations associated with injury are resisted with much more force. Therefore, the brace is only limiting motion for kinesiological actions associated with injury.

In addition, and more subtly, a rate-dependent, elastically-deformable device 10 may be effective for reducing the likelihood or severity of injury if it merely acts to slow the supination action. This hypothesis is based on the observation that many injuries increase in likelihood when the individual becomes tired, and the corresponding nervous-muscular response times of the joints lag accordingly. In this scenario, when supination begins the opposing muscles have the capacity to resist over-rotation of the joint, but due to fatigue do not react in time to prevent injury. A rate-dependent, elastically-deformable device 10 that acts on the ankle to slow rotation, providing only a fraction of a second of additional reaction time, could be effective at allowing the body's built-in musclature to resist the injurious rotation.

Figure 6A:
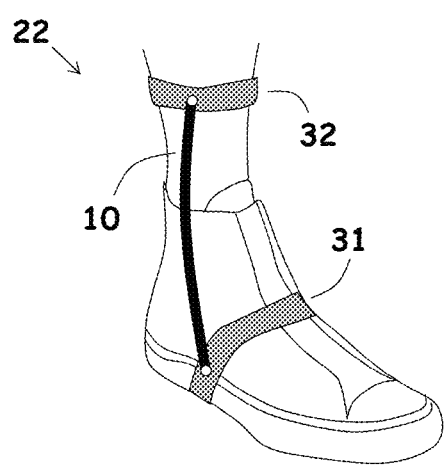
FIGS. 6A-6D illustrate an ankle orthotic comprising a rate-dependent, elastically-deformable device coupled between the foot and a cuff above the ankle, where

An ankle brace that that has one or more rate-dependent, elastically-deformable devices 10 mounted in various configurations functions to alleviate unwanted ankle supination. For example, in a first embodiment, a rate-dependent, elastically-deformable device 10 could be mounted between a cuff on the shank (or lower leg) to the side of the shoe to limit unwanted ankle supination. An example of such an orthotic 22 is shown in FIG. 6A, with foot cuff 31 and shank cuff 32. These cuffs could include, for example, a hook-and-loop fastener (Velcro®) strap, a strap with a buckle, or a laced harness. The device 10 can be mounted and attached to the cuff using one of an attachment hole, pin, knot, rivet, adhesive, or friction joint. The foot cuff could be designed to retrofit to a shoe, such as by engaging the sole of the shoe, or mounting to an eyelet. While walking, the device will not apply a force so that the user muscles do not weaken over time accommodating to the additional strength added in parallel to the ankle muscular tendon structure if a standard elastic device is used. However, when the ankle supinates quickly, an additional force from the device 10 will limit unwanted ankle supination.

Figure 6B:
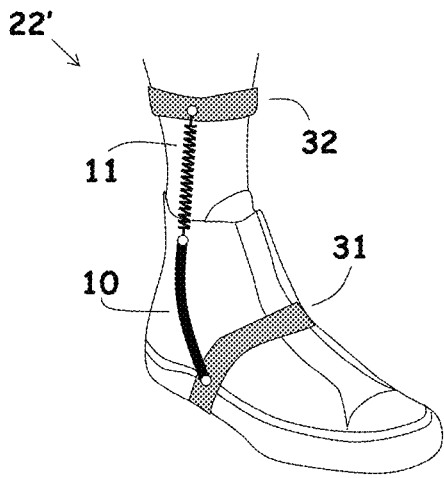
Figure 6C:
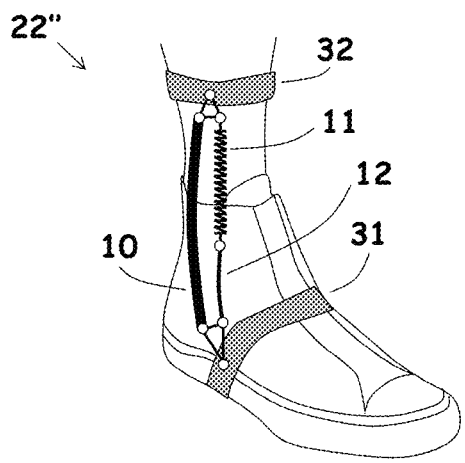
Figure 6D:
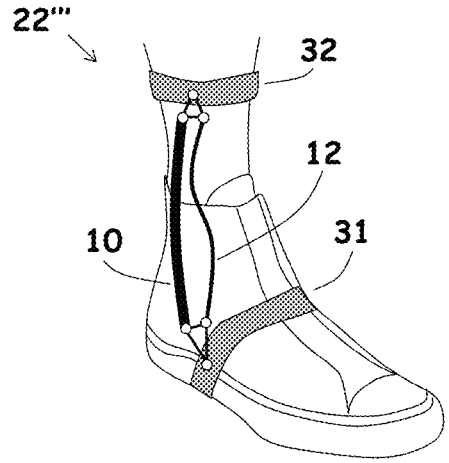

In a second embodiment, the device 10 can be mounted in series with elastic elements to tune the stiffness of the band mounted to the wearable device. FIG. 6B shows such an orthotic 22', in which the device 10 is in series with an elastic spring 11. The elastic spring could be composed of, for example, plastic or metal, could be coil spring, or could be an elastic strap or rubber band. In a third embodiment, the device 10 can be mounted in parallel with elastic elements to tune the stiffness of the band mounted to the wearable device. FIG. 6C shows such an orthotic 22", in which the elastic element 11 is in series with an inextensible filament 12, and this sub-assembly is in parallel with the device 10. This inextensible filament 12 could be, for example, a metal or plastic cable or rope, and woven fabric strap, a plastic ribbon, a metal ribbon, or a chain. In a fourth embodiment, the device 10 can be mounted in parallel to a rigid band/cable that is slack during normal walking and motion but limits the total supination angle to a pre-defined angular value such as thirty degrees. FIG. 6D shows an orthotic 22", in which the inextensible filament 12 is a cable that limits total ankle rotation. In summary, one or more devices 10 can be mounted in parallel with or in series with springs, bungee cords, cables, fasteners, elastic bands, tape and other common bracing materials.

Figure 7:
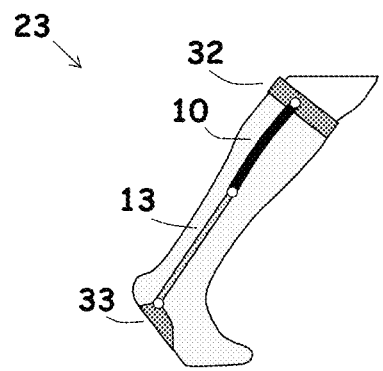
FIG. 7 shows a specific ankle brace embodiment, in which a cuff is located above the calf muscle but below the knee, this cuff is coupled to one end of a rate-dependent, elastically-deformable device, the other end of the device couples to one end of an inextensible flexible strap, and the other end of the flexible strap couples to the foot via a semi-rigid plastic support piece worn under the arch of the foot.

FIG. 7 shows an ankle orthotic 23 in which the device 10 is in series with an inextensible, flexible strap 13. The device 10 is coupled to a shank cuff 32, located above the calf muscle to provide a solid anchoring point for resisting downward force. The inextensible, flexible strap 13 is anchored to an underfoot support 33, which could be a semi-rigid fabric or plastic sheet that is designed to fit between the bottom of the foot and the top of a shoe sole when the user is wearing a shoe. The entire orthotic may be packaged within a knitted or compression sock, and the cuff 32, device 10, and inextensible strap 13 may be coupled to the sock via sewing, stitches, rivets, adhesives or other commonly used fixation techniques. The device 10 and inextensible, flexible strap 13 may be further guided within a tube of fabric sewn into the sock, or may be supported with padding to increase comfort in some implementations.

Figure 8:
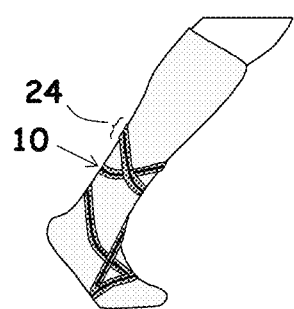
FIG. 8 shows ankle support provided by a wrap containing incorporated rate-dependent, elastically-deformable devices.

The device 10 can be mounted in parallel or in series with elastic bands, and tape. For example, in an embodiment, the device 10 can be integrated into an elastic band. It might be sewn into the band, glued or attached appropriately, for instance. The new rate resistant band could be used to wrap on to a joint of an individual to limit unwanted motion. The band could be wrapped on to the ankle, knee, elbow, wrist, finger or any joint. FIG. 8 shows one possible wrapping configuration for ankle support, in which the wrap assembly 24 is comprised of an elastic band, such as an elastic bandage, with a device 10 integrated into the material.

In another embodiment, a device 10 will be taped to an ankle joint with athletic tape. The device 10 will be mounted across the ankle joint to limit unwanted supination movement. At one side of the device 10, it can be taped to the shank or calf. At a second side, it can be taped to the side of the foot. The device 10 can be taped in multiple spots to ensure that it does not move. All types of mounting can be envisioned such as the device 10 mounted with (and sold with the tape for that purpose). The device 10 can be mounted in the athletic tape sandwiched between pieces of tape. The tape can have slots cut into it, with the device 10 mounted in the slots to bridge the gaps.

The orthotic device embodiments can be used to restrict motion of an animal or human joint. The embodiments may provide comfort to race animals like horses and dogs. For example, a band could be wrapped on the joints of a horse or dog etc. Sizing and customization of an orthotic device for a particular patient will likely be performed by a physician or veterinarian as typical for medical devices.

Although ankle supination is the most common type of ankle injury, other modes of injury such as ankle pronation are also possible. Ankle orthotics with rate-dependent, elastically-deformable devices could be configured to resist supination, pronation, or both injury modes. For example, the orthotic examples in FIGS. 6A-6D have devices on the outer face of the ankle, which would position them most suitably to resist ankle supination. Similar device arrangements placed on the inner face of the ankle would help to reduce ankle injury from pronation. Devices placed on both sides of the ankle would result in an orthotic that would be reduce the likelihood of both supination and pronation injuries.

Figure 9:
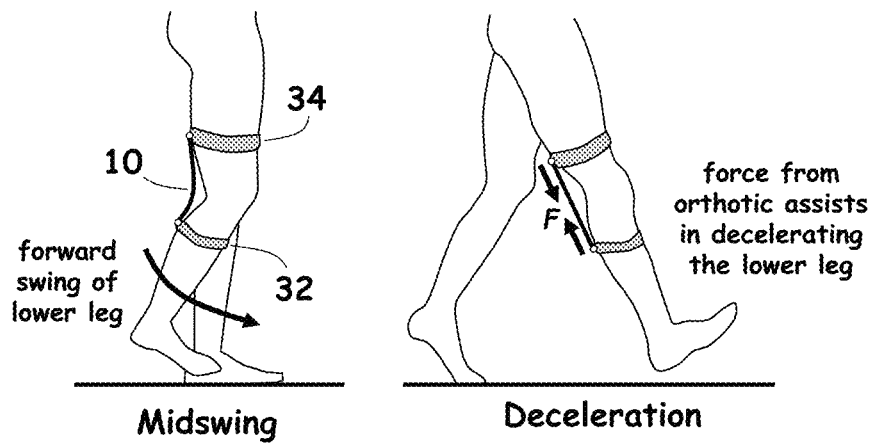
FIG. 9 shows a knee orthotic that decelerates the lower leg at the end of the forward swing phase of a walking gait, reducing the muscle activity required for the wearer.

For human performance enhancement, it is known that energy is required to slow the leg as it swings forward in the air at the end of the gait cycle. A simple elastic band connected between the back of the shank and the hips, as a simple example, would in principle assist in reducing the effort required during stride recovery. However, this elastic band also provides continuous resistance, whether walking or running, which may not be optimal at all speeds. FIG. 9 shows how force application could be used to decrease metabolic energy expenditure during walking using a rate-dependent, elastically-deformable device 10. A rate-dependent, elastically-deformable device 10 connected between the hip and shank, using a thigh cuff 34 and shank cuff 32 to couple to the wearer, perhaps in series or in parallel with inextensible or elastic bands, would permit a differently tuned response during walking and running strides. For example, the device 10 could be designed and constructed for low stride manipulation during walking, but provides much more significant leg assistance during higher speed running strides. This stride speed tailorability could enable smart, tailorable stride modification in a compact, self-powered, robust wearable ensemble.

Figure 10:
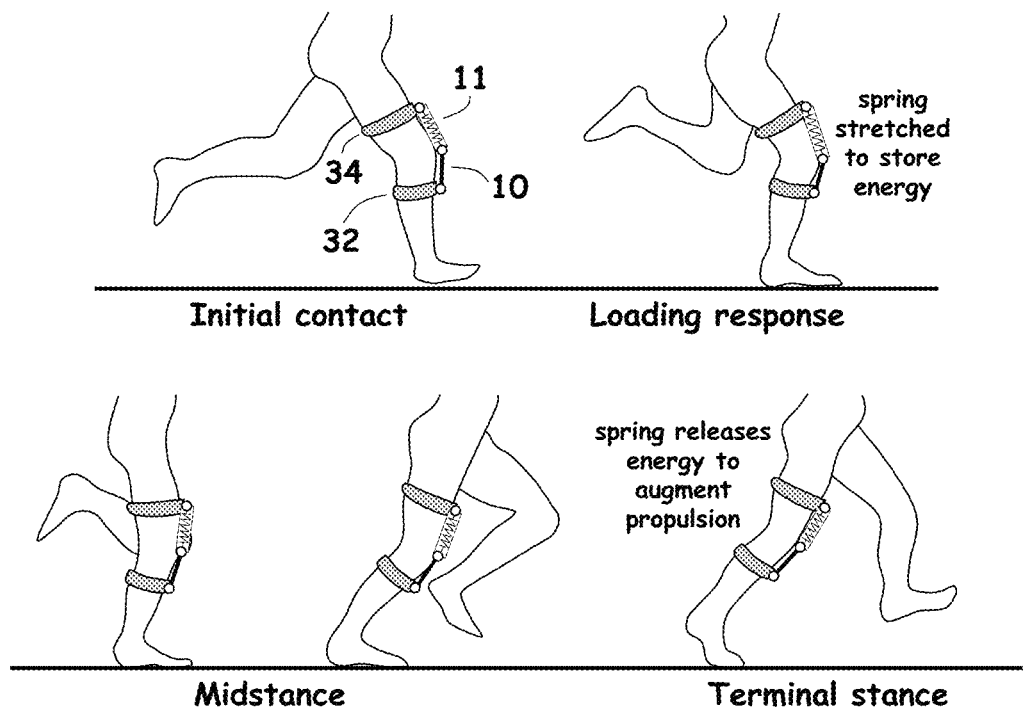
FIG. 10 is a schematic showing the different phases of a running gait, and shows how a knee orthotic comprising at least one rate-dependent, elastically-deformable device coupled between the thigh and shank, and comprising an elastic spring, can be used to store and release energy to enhance gait efficiency.

In another example, for human performance enhancement, it is known that energy is required to flex and extend the knee after heel strike when walking and running. A simple elastic band connected at the front of the knee across the shank and the thigh, as a simple example, would in principle assist in reducing the effort required. However, this elastic band also provides continuous resistance, whether walking or running, that may not be optimal at other parts of the gait cycle or at all speeds. FIG. 10 shows how force application during running could be used to improve biomechanical efficiency and performance using a rate-dependent, elastically-deformable device 10. A device 10 connected between the thigh and shank, perhaps in series or in parallel with inextensible or elastic bands 11, would permit a differently tuned response during walking and running strides. For example, the device 10 could be designed to not function at slow speeds, such as while walking, but provide a spring force when jogging or running. This stride speed tailorability could enable smart, tailorable stride modification in a compact, self-powered, robust wearable ensemble.

In this example, an extension spring in series with a rate-dependent, elastically-deformable device 10 could be tailored to provide assistance when running. At slow speeds, the device 10 would stretch and provide little resistance and no energy would be stored in the series-spring. At high speeds, the device 10 would resist movement allowing the series-spring to stretch when the knee flexes and then return the energy to the leg as the knee extends. This energy storage and return mechanism of the series spring can be used at high speeds and not at slow walking speeds. The device 10 would act as a clutch to turn on the energy storage mechanism at high speeds.

A second clutch would be needed to in the swing phase of walking and running to eliminate any resistance as the knee flexes. To reduce any unwanted forces, the rate-dependent, elastically-deformable device combined unit would need to be removed from the load path during the swing phase of gait.

Figure 11A:
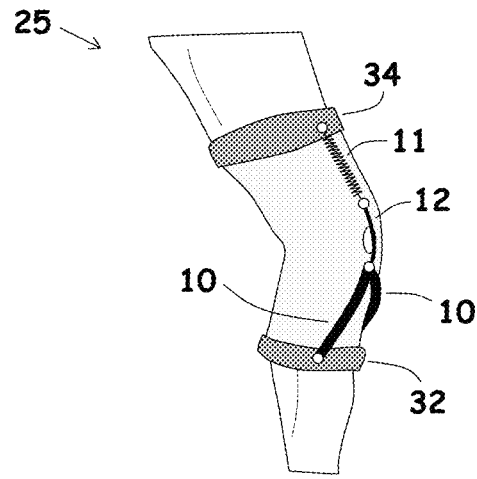
FIGS. 11A-11C show knee orthotics comprising rate-dependent, elastically-deformable devices coupled between the thigh and shank, where in FIG. 11A two parallel devices are in series with a longitudinally elastic spring, configured to resist knee flexure.

In this knee device, multiple configurations could be used. A simple extension spring could be combined with a rate-dependent, elastically-deformable device 10. FIG. 11A shows one such knee orthotic 25. An elastic spring 11 is in series with an inextensible cable 12, which is then mounted to two devices 10 in parallel. The devices 10 are then coupled to a shank cuff 32, and the elastic spring is affixed to the wearer via a thigh cuff 34. The properties of the rate-dependent, elastically-deformable device 10 and spring properties could be tuned so that knee flexure at low speeds, such as during walking, results in extension of the device 10 without spring elongation and overall low resistance to bending. In contrast, knee flexure at high speeds, such as during running, results in spring elongation during contact and loading portions of the running stride, with the spring then elastically recovering and assisting with knee flexure during midstance and terminal stance. Slowing the knee flexion when the leg touches the ground and the knee is flexed will reduce the negative work needed reducing fatigue and metabolic cost. The device 10 can be mounted across the knee joint in many different ways using athletic tape, braces, orthotics, etc.

Figure 11B:
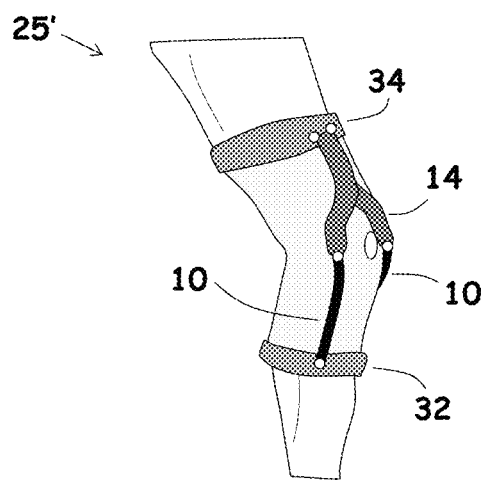

In a second configuration, the devices 10 could be combined with elastic bending elements, such as a leaf spring or lightweight composite beam. FIG. 11B shows such an orthotic 25'. A y-shaped leaf spring 14 is mounted on the front of the thigh, above the knee, and is coupled to two parallel devices 10. During slow knee flexure, the devices 10 stretch and the leaf spring does not bend. During rapid knee flexure, the devices 10 resist elongation, and the leaf springs bend. During subsequent knee extension, the leaf springs would recover, providing mechanical assistance to the leg as it straightens.

In another embodiment, the rate-dependent, elastically-deformable device 10 can be mounted in conjunction with a knee orthotic to limit knee flexion when sitting down. When the knee bends and flexes, the device 10 would be stretched. As the person sits down quickly and the knee is flexed, the device 10 is stretched quickly. When the knee flexes quickly, resistance is felt and the negative work done by the muscles acting at the knee will be reduced. The device 10 will allow one to sit slowly and comfortably in a chair. Once the motion is complete, the device 10 will relax and the resistance is no longer felt. This relaxation after the completed movement is very important. In a standard spring based system, the knee movement in a sitting task can be resisted, but the spring is in a loaded state when sitting, pulling on the user in an uncomfortable situation. In the present embodiment, the reduction of the potential energy when sitting is absorbed and resisted by the device 10. The device 10 will resist the movement and heat up absorbing energy. In a standard spring based device, the reduction of the potential energy as the weight of the body is lowered is transferred to spring energy. The spring energy must be clutched for other uses, released, or forces the leg into a straight position. The device 10 can be mounted across the knee joint in many different ways using athletic tape, braces, orthotics, compression sleeves etc.

Figure 11C:
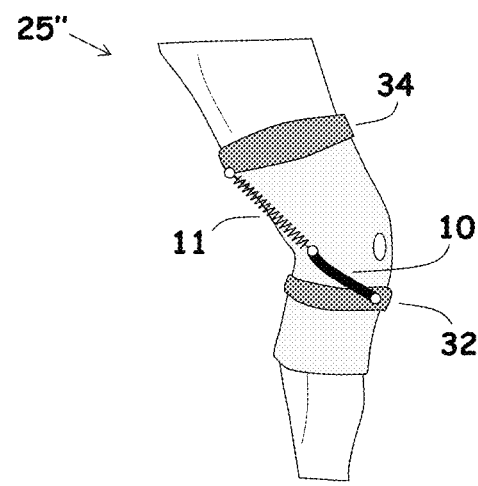

In another configuration, the devices 10 are used to improve efficiency during leg swing. FIG. 11C shows a knee orthotic 25", having an elastic element 11 in series with a rate-dependent, elastically-deformable device 10. The elastic element is affixed to the body toward the rear of the thigh via the thigh cuff 34, while the device 10 is affixed to the body near the front of the shank via the shank cuff 32. A symmetric arrangement of elements could also be in place on the opposite side of the same leg, although it is not visible in this figure. During low speed walking, the device 10 provides low resistance, and the spring is not extended, resulting in low walking resistance. During running, the device 10 resists extension, so that knee extension causes the spring to stretch, providing force that decelerates the shank as it swings forward. This action reduces the muscle activity normally required to bring the shank to a state of low angular velocity. As the knee is then placed into flexure later in the gait, the stored energy in the spring can be used to provide a restorative torque that assists with flexure, further reducing metabolic cost and increasing stride efficiency.

Similar rate-dependent, elastically-deformable devices and elastic element configurations could be used in an orthotic between the hip and thigh, to increase stride efficiency by aiding deceleration during leg swing, and returning energy to the leg to augment propulsion.

For circulation-enhancing compression garments, a rate-dependent, elastically-deformable device 10 could enable enhanced compressive action during muscle actuation, with reduced stress during muscle relaxation for comfort. Consider a tight-fitting calf compression sock integrated with one or more devices 10. The elastic resistance during a static, relaxed state would be low, due to the low force resistance of the device 10 at low speeds. However, if the wearer were to flex their calf muscle quickly, such as by lifting one's toes off the ground, the increasing girth of the tensed muscle would be restricted by the device 10, leading to high compression on the calf. In this design, the device 10 allows the wearer to create momentary bursts of high compression via muscle flexing, followed by periods of comfortable, low compression. During walking, this sequence of flexing and relaxation would lead to a consistent pattern of pulsed compression on the calf, enhancing circulation while remaining comfortable. In non-limiting examples, these devices could worn by passengers on airplanes by users with poor blood circulation, and users suffering from diabetes.

The device 10 can be mounted in conjunction with a circulation-enhancing calf compression sleeve. For example, device 10 would be mounted in the back of the calf (or shank) surrounding the gastroc and soleus muscle. The device 10 can be mounted vertically, horizontally, or at an angle in a preferred comfortable pattern. As the muscle expands and contracts when walking, pressing the foot against the ground, lifting the toe up or other joint motions, the device 10 would stiffen and then release during the joint motion to help pump the blood flow.

Figure 12A:
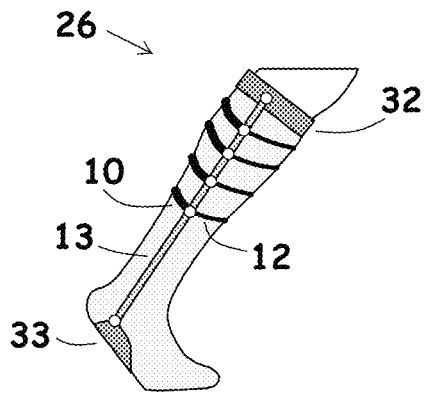
FIGS. 12A-12C show a compression orthotic with rate-dependent, elastically-deformable devices integrated to create constrictive pressure on the calf during muscle activation, where FIG. 12A uses an array of devices positioned around the calf muscle to induce pressure.

FIG. 12A shows one embodiment of a circulation-enhancing lower leg orthotic 26. An array of parallel devices 10 are configured to stretch when the calf muscles expand. They are coupled to a flexible or semi-flexible strap 13, and further braced to the upper shank via a series of inextensible cables or straps 12. The assembly is held in place with an upper shank cuff 32 and an underfoot support 33. If the calf is relaxed, the device 10 are in a state of low elongation and low pressure is provided. However, if the calves are quickly flexed, the devices 10 resist muscle radial expansion, inducing a radial compressive pressure that momentarily enhances blood pressure in the calf to assist in pumping venous blood back to the heart.

Alternatively, a braided mesh sleeve (similar to those used in McKibben pneumatic actuators) could be wrapped around the calf. This braided mesh would be constructed so that, when tensioned longitudinally, it contracts radially and generates a radial compressive force on the shank. The mesh would be fixed on its lower end to the foot, and on its upper end to the upper shank, knee and/or thigh via a rate-dependent, elastically-deformable device. During walking or running, tension would be generated in the device, contracting the mesh and generating radial compression on the calf to enhance circulation.

Figure 12B:
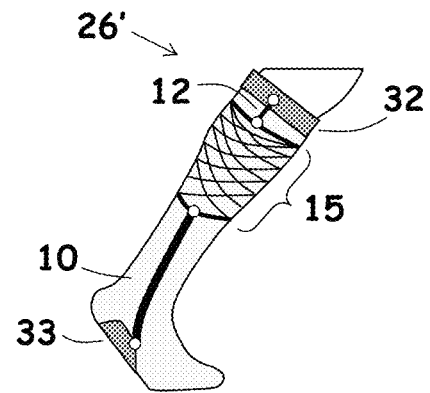

FIG. 12B shows another embodiment of a circulation-enhancing lower log orthotic 26". A braided mesh 15 is placed around the calf, and is tensioned between a device 10 and an inextensible element 12. During low speed ankle extension, the device 10 extend with low resistance, resulting in low tension on the mesh and low radial compression on the calf. During brisk walking or rapid ankle extension, the device 10 resist extension, transmitting high tension to the mesh, resulting in radial contraction of the mesh and generating pressure on the calf. Cessation of motion at any time causes the device 10 to relax, allowing the mesh to expand and reducing calf pressure.

Figure 12C:
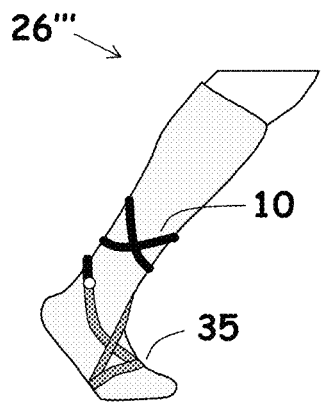

FIG. 12C shows another embodiment of lower leg orthotic 26''', in which a device 10 is coupled in series with an inextensible banding or tape 35 which is wrapped around the foot and ankle. The banding and device 10 can be adjusted and fit using adhesive, tape, hook-and-loop fasteners, pins, or other common fixation techniques. During foot flexure or calf activation, the device 10 resist calf expansion, generating pressure on the calf that enhances blood circulation.

The orthotics such as described in FIGS. 12A-12C may be packaged within a knitted or compression sock, and the cuffs, rate-dependent, elastically-deformable devices, mesh, and inextensible straps may be coupled to the sock via sewing, stitches, rivets, adhesives or other commonly used fixation techniques. The rate-dependent, elastically-deformable devices, mesh, and inextensible straps may be further guided within a tube of fabric sewn into the sock, or may be supported with padding to increase comfort.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, to thereby enable others skilled in the art to best utilize the invention and various embodiments with various modifications as may be suited to the particular use contemplated.

While the foregoing is directed to embodiments of the present invention, other and further embodiments of the invention may be devised without departing from the basic scope thereof, and the scope thereof is determined by the claims that follow.

We claim:

1. An ankle orthotic device to be worn by a wearer comprising:
   a coupling element configured to couple to the lower leg of the wearer;
   a coupling element configured to couple to the foot of the wearer; and
   at least one rate-dependent, elastically-deformable device coupled to at least one of the coupling elements,
      wherein the orthotic is configured to resist ankle supination and/or ankle plantarflexion, and
      wherein the at least one rate-dependent, elastically-deformable device comprises:
   (i) an elastic-deformable confinement member, (ii) one or more filaments placed inside the confinement member, (iii) end effectors connected to the confinement member and couple to the one or more filaments; (iv) a shear-thickening fluid (STF) that fills the confinement member and wets the one or more filaments.

2. The device of claim 1, wherein the lower leg coupling element comprises a cuff, a tape, a bandage, a sleeve, or a compression fabric.

3. The device of claim 2, wherein the lower leg coupling element is mounted above the calf and below the knee.

4. The device of claim 2, wherein the sleeve is a sock.

5. The device of claim 1, wherein the foot coupling element is placed under the foot and above the sole of a shoe or other footwear.

6. The device of claim 1, further comprising at least one elastic element in series with the at least one rate-dependent, elastically-deformable device.

7. The device of claim 1, further comprising at least one elastic element in parallel with the at least one rate-dependent, elastically-deformable device.

8. The device of claim 1, further comprising at least one cable or restrictive element in parallel with the at least one rate-dependent, elastically-deformable device.

9. A knee orthotic device to be worn by a wearer comprising:
   a coupling element configured to couple to the upper leg of the wearer;
   a coupling element configured to couple to the lower leg of the wearer; and
   at least one rate-dependent, elastically-deformable device coupled to at least one of the coupling elements,
      wherein the at least one rate-dependent, elastically-deformable device comprises: (i) an elastic-deformable confinement member, (ii) one or more filaments placed inside the confinement member, (iii) end effectors connected to the confinement member and couple to the one or more filaments; (iv) a shear-thickening fluid (STF) that fills the confinement member and wets the one or more filaments.

10. The device of claim 9, where the orthotic is configured to modify walking or running by the wearer.

11. The device of claim 9, where the orthotic device absorbs energy during knee flexion while the leg is in contact with the ground.

12. The device of claim 9, where the orthotic device stores elastic energy during one part of the stride, and then releases the energy to assist with locomotion during another part of the stride.

13. The device of claim 9, further comprising at least one elastic element in series with the at least one rate-dependent, elastically-deformable device.

14. The device of claim 9, further comprising at least one elastic element in parallel with the at least one rate-dependent, elastically-deformable devices.

15. The device of claim 9, where the orthotic device is configured to resist knee hyperextension.

16. A lower leg orthotic device to be worn by a wearer, comprising
   a coupling element configured to couple to the lower leg of the wearer; and
   at least one rate-dependent, elastically-deformable device,
      wherein the at least one rate-dependent, elastically-deformable device is configured to induce pressure on the lower leg to enhance blood circulation of the wearer, and
      wherein the at least one rate-dependent, elastically-deformable device comprises:
   (i) an elastic-deformable confinement member, (ii) one or more filaments placed inside the confinement member, (iii) end effectors connected to the confinement member and couple to the one or more filaments; (iv) a shear-thickening fluid (STF) that fills the confinement member and wets the one or more filaments.

17. The device of claim 16, wherein the at least one rate-dependent, elastically-deformable device induces pressure in the wearer's leg when the wearer walks or runs.

18. The device of claim 16, where the coupling element comprises a sleeve that surrounds the calf muscle, wherein the braided mesh sleeve radially contracts due to longitudinal tension.

19. The device of claim 18, wherein the longitudinal tension is generated by the at least one rate-dependent, elastically-deformable device in series with the sleeve.

20. The device of claim 18, wherein the sleeve is a sock.

21. The device of claim 16, wherein the at least one rate-dependent, elastically-deformable device is arranged to resist muscle flexure.

* * * * *